United States Patent [19]
Fukaya et al.

[11] Patent Number: 5,393,397
[45] Date of Patent: Feb. 28, 1995

[54] OXYGEN SENSOR

[75] Inventors: Tomoji Fukaya, Kariya; Masahiro Shibata; Kazunori Suzuki, both of Nagoya; Makoto Nakae, Toyoake; Syuichi Nakano, Kariya; Masatoshi Suzuki, Nagoya, all of Japan

[73] Assignee: Nippondenso Co., Ltd., Kariya, Japan

[21] Appl. No.: 172,222

[22] Filed: Dec. 23, 1993

[30] Foreign Application Priority Data

Dec. 25, 1992 [JP] Japan .................. 4-359200

[51] Int. Cl.$^6$ .................................... G01N 27/26
[52] U.S. Cl. ...................... 204/424; 204/426; 204/425; 204/427
[58] Field of Search ............... 204/424, 425, 426, 427, 204/418, 283, 295

[56] References Cited

U.S. PATENT DOCUMENTS

| | | | |
|---|---|---|---|
| 5,037,525 | 8/1991 | Badwal | 204/427 |
| 5,124,021 | 6/1992 | Kaneyasu et al. | 204/425 |
| 5,137,615 | 8/1992 | Friese et al. | 204/425 |
| 5,273,628 | 12/1993 | Friese et al. | 204/283 |

FOREIGN PATENT DOCUMENTS 1227956 9/1989 Japan .

Primary Examiner—John Niebling
Assistant Examiner—Bruce F. Bell
Attorney, Agent, or Firm—Cushman, Darby & Cushman

[57] ABSTRACT

An oxygen sensor capable of accelerating electrochemical reactions and practically working at a low temperature comprises a solid electrolyte 5, and an outer electrode 31 and an inner electrode 32, provided on the surfaces of the solid electrolyte 5, wherein mixed conductors 11 and 12 capable of adsorbing oxygen molecules and conducting an ionization reaction are provided between the solid electrolyte 5 and the outer electrode 31 and between the solid electrolyte 5 and the inner electrode 32, respectively. The mixed conductors 11 and 12 are porous and have a higher oxygen ion conductivity than that of the solid electrolyte 5 and an electron conductivity substantially equivalent to the oxygen ion conductivity and are made of a fluorite-type oxide or a perovskite-type oxide.

8 Claims, 8 Drawing Sheets $i\ell$ : LIMITED CURRENT
Vo : DETECTED POTENTIAL

FIG. 12C
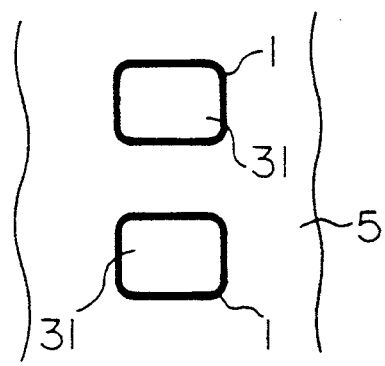
FIG. 13
ADSORPTION REACTION $\quad O_2 + \bullet \rightarrow (O_2 - \bullet)_{ADSORBED}$
DISSOCIATION REACTION $\quad (O_2 - \bullet)_{ADSORBED} \rightarrow 2(O - \bullet)_{ADSORBED}$
IONIZATION REACTION $\quad 2(O - \bullet)_{ADSORBED} + 2e^- \rightarrow (O^{2-} - \bullet)_{ADSORBED}$
ION MIGRATION $\quad (O^{2-} - \bullet)_{ADSORBED} \rightarrow O^{2-} + \bullet$
( $\bullet$ : TERNARY PHASE BOUNDARY POINT )
FIG. 14
PRIOR ART
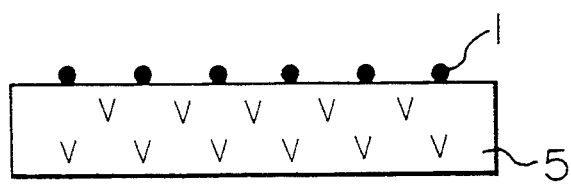

OXYGEN SENSOR

BACKGROUND OF THE INVENTION

1. Field of the Invention

The present invention relates to an oxygen sensor for use in control of air/fuel ratio in combustion engines for automobiles, for instance.

2. Related Prior Art

So far known practical oxygen sensors for detecting an oxygen concentration of exhaust gas from automobile internal combustion engines are usually of electromotive force type, oxygen ($O_2$) pumping current type, limited current type, etc.

The oxygen sensor of electromotive force type is to detect an oxygen concentration by comparing changing potentials by an oxygen ionization reaction with a reference potential.

The oxygen sensor of $O_2$ pumping current type is to measure an oxygen ion electromotive force generated between solid electrolytes, for example, oxygen ion-conducting, stabilized zirconia-based solid electrolytes ($ZrO_2$—$Y_2O_3$, etc.), when a current is passed therebetween.

The oxygen sensor of limited current type is to measure an oxygen ion current passing through a solid electrolyte by applying a voltage thereto and limiting the thus generated oxygen ion current by a diffusion-resistant layer.

As shown in FIG. 8, the oxygen sensor of limited current type has a sensor element 90 at its tip end. The sensor element 90 is a cup-formed element, as shown in FIGS. 8 and 9, which is formed by laminating an inner electrode 32, a $ZrO_2$ solid electrolyte 5, an outer electrode 31 and a diffusion-resistant layer 2 successively from the inside outwardly. A heater 6 is inserted into the inner cavity 901 of the sensor element 90. An insulating layer 4 is provided between the outer periphery of the solid electrolyte 5 and the diffusion-resistant layer 2 except the site for the outer electrode 31.

The outer electrode 31 and the inner electrode 32 are connected to a connector 98 above the sensor element 90 through lead wires 91 and 92, respectively. These two electrodes are porous platinum electrodes, or the like. The heater 6 is connected to the connector 98 through a lead wire 93.

The insulating layer 4 is made of an insulator and sets an electrode area, thereby controlling an output current density. The diffusion-resistant layer 2 serves to protect the outer electrode and also control a limited current.

The sensor element 90 is fixed to an exhaust gas pipe, etc. by a flange 97 provided at a housing 96. A protective cover 95 is provided at the outside of the sensor element 90.

When a voltage is applied between the outer electrode 31 and the inner electrode 32 in the oxygen sensor 9, electro-chemical reactions take place between these two electrodes, and an oxygen concentration can be determined by detecting a current passing therebetween due to the reactions. Relations between the applied voltage and the output current are shown in FIG. 11.

The electrochemical reactions proceed while transferring electrons between the cathode (outer electrode) and the anode (inner electrode) by oxygen, as shown in FIG. 12A. That is, as shown in FIGS. 12B, 12C and 13, oxygen molecules ($O_2$) contained in a gas phase are adsorbed on the three-phase boundary points 1 between the outer electrode 31, the solid electrolyte 5 and the gas phase.

The oxygen molecules ($O_2$) adsorbed on the three-phase boundary points 1 are dissociated into oxygen atoms (O). The dissociated oxygen atoms (O) receive electrons ($e^-$) from the outer electrode 31 and are ionized, while leaving the three-phase boundary points 1 as oxygen ions ($O_{2-}$). The oxygen ions ($O_{2-}$) migrate through the solid electrolyte 5, as shown in FIG. 12B, and reach the three-phase boundary points between the inner electrode 32, the gas phase and the solid electrolyte 5, where the oxygen ions ($O_{2-}$) give electrons ($e^-$) to the inner electrode 32. The electrochemical reactions take place in this manner.

The rate-determining step in the electrochemical reactions is an adsorption reaction of oxygen molecules onto the three-phase boundary points 1. To facilitate the adsorption it would be possible to make the outer electrode 31 porous, thereby increasing the number of the three-phase boundary points 1. However, as shown in FIG. 14, even if the number of the three-phase boundary points is increased, there is no change in the volume each of the individual three-phase boundary points 1. Furthermore, the ternary phase boundary points 1 are formed only on the surface of the solid electrolyte 5, and thus there is a limit to the available number of the three-phase boundary points.

To practically keep the oxygen sensor operative, both electrodes must be heated to a high temperature such as 700° C. by the heater 6. Heat loss is large due to the working at such a high temperature, resulting in large power consumption of the heater 6.

SUMMARY OF THE INVENTION

An object of the present invention is provide an oxygen sensor capable of promoting electrochemical reactions and working practically at a low temperature, while solving the problems so far encountered.

According to the present invention there is provided an oxygen sensor which comprises a solid electrolyte and electrodes provided on surfaces of the solid electrolyte, wherein a mixed conductor capable of adsorbing oxygen molecules and conducting an ionization reaction is provided between the solid electrolyte and each of the electrodes.

DETAILED DESCRIPTION OF THE INVENTION

In the present invention, the mixed conductor is made of a substance capable of making ions and electrons participate in electroconduction. The mixed conductor plays a role of electrode reaction layer capable of adsorbing oxygen molecules and conducting an ionization reaction between the solid electrolyte and the electrodes. Furthermore, the mixed conductor is porous and has a higher oxygen ion conductivity than that of the solid electrolyte and also an electron conductivity substantially equivalent to the oxygen ion conductivity. The electron conductivity of the mixed conductor is preferably based on the n-type semiconductivity. Still furthermore, the mixed conductor has preferably a good adhesion to the solid electrolyte, and the crystal system and the coefficient of thermal expansion of the mixed conductor are preferably similar to those of the solid electrolyte, because of improvement in physical properties and maintenance of the strength of the mixed conductor.

Examples of the mixed conductor includes perovskite type oxides, fluorite type oxides, etc.

Chemical compositions of the perovskite type oxides include, for example, $La_{1-x}Sr_xCoO_3$, $Nd_{1-x}Sr_xCoO_3$, $Nd_{1-x}Ca_xCoO_3$, $La_{1-x}Sr_xNiO_3$, etc.

Chemical compositions of the fluorite type oxides include, for example, $Ce_{1-x}La_xO_3$, $Ce_{1-x-y}(M_2O_3)_x$, $(M'_2O_5)_y$, etc., wherein x is not more than 0.5; y is not more than 0.03; M is one of trivalent metal elements such as $Ca^{3+}$, $Y^{3+}$, $Yb^{3+}$, $Gd^{3+}$, etc.; M' is one of pentavalent metal elements such as $Nb^{5+}$, $Ta^{5+}$, etc.

When x exceeds 0.5 or when y exceeds 0.03, there is a possibility that the ion conductivity of the mixed conductor will be decreased.

When the fluorite type oxide is used as a mixed conductor, there is a possibility that the n-type semiconductivity of the mixed conductor will be decreased with increasing oxygen partial pressure and consequently the electron conductivity will be lowered.

Thus, it is necessary to increase a concentration of excess electrons of the mixed conductor within such a range as not to give an adverse effect on the oxygen ion conductivity, thereby assuring a high electron conductivity. From this point of view, it is desirable that the mixed conductor contains a very small amount of pentavalent metal such as $Nb^{5+}$, $Ta^{5+}$, etc., for example, $(CeO_2)_{0.915}(Gd_2O_3)_{0.08}(Nb_2O_5)_{0.005}$.

It is preferable that the mixed conductor has a porosity of 20 to 40%. Below 20%, the mixed conductor will have a problem in the oxygen permeability, whereas above 40% the mixed conductor will have a problem in the physical strength. It is preferable that the mixed conductor has a layer thickness of not more than 25 $\mu$m. Above 25 $\mu$m, the oxygen permeability will be deteriorated. The mixed conductor can be applied in a layer thickness of not more than 5 $\mu$m by sputtering. The smaller the layer thickness of the mixed conductor, the more improved the oxygen permeability.

The solid electrolyte can pass only oxygen ions, but not electrons. Examples of the solid electrolyte include $ZrO_2$-based oxides. Electrodes for use in the present invention includes, for example, a porous platinum electrode, etc. Other materials are the same as so far employed.

A process for producing an oxygen sensor according to the present invention will be outlined below, referring to one example.

At first, a predetermined amount of acetates of metallic elements for constituting a mixed conductor is dissolved into a predetermined amount of water and the resulting solution is dried and solidified at a temperature of about 60° C. to about 100° C. under reduced pressure. The solidified dry matters are heated to 200° C. to decompose the acetates of metallic elements. The decomposition product is pulverized and fired at a temperature of 900° C. to 1,100° C. in air, thereby obtaining powder of mixed conductor. Then, the powder is made into a paste, thereby obtaining a mixed conductor paste.

Then, the mixed conductor paste is applied to the surfaces of a calcined body of solid electrolyte destined to an oxygen sensor by printing, sputtering or the like. Then, electrodes of platinum, etc. are deposited on the surfaces of the mixed conductor by paste application, plating, or the like, and then baked.

Then, an insulating layer and a diffusion-resistant layer are formed on the outer surface of the solid electrolyte, thereby making a sensor element. Then, the sensor element is mounted to complete an oxygen sensor.

According to another process, the mixed conductor paste is applied to the surface of a green sheet of solid electrolyte. After firing, the electrode paste is applied thereto, followed by baking.

The present oxygen sensors can be utilized as oxygen sensors of limited current type, $O_2$ pumping current type, etc.

The oxygen sensor of limited current type is in a monocellular structure of porous type, or of hole type, where a pinhole or a slit is provided through the solid electrolyte. The oxygen sensor of $O_2$ pumping current type is in a bicellular structure of the same porous type or hole type as above.

According to the present invention, a mixed conductor capable of adsorbing oxygen molecules and conducting an ionization reaction is provided between the solid electrolyte and each of the electrodes (cathode and anode). Thus, when the oxygen sensor is placed in an oxygen gas-containing atmosphere, oxygen molecules are permeated into the mixed conductor in contact with the cathode. The permeated oxygen molecules are adsorbed in the mixed conductor and dissociated into oxygen atom while maintaining the adsorbed state. The dissociated oxygen atoms receive electrons from the electrode and ionized and leave the mixed conductor as oxygen ions.

In the present invention, it should be noted that a series of reactions such as the adsorption reaction, dissociation reaction, ionization reaction and leaving reaction take place not only on the surface of the mixed conductor, but also inside the mixed conductor. That is, in the present invention, three-phase boundary points (between electrode, gas phase and solid electrolyte) for conducting the reactions are formed inside the mixed conductor and thus the reactions proceed at every sites, that is, three-dimensional sites, in the mixed conductor.

In the conventional oxygen sensor, on the other hand, the three-phase boundary points exist only at the contact points between the solid electrolyte and the outer peripheries of the electrodes in contact with the solid electrolyte. That is, the three-phase boundary points are formed only at the circular sites of the outer peripheries of electrodes. Thus, the three-phase boundary points of the conventional sensor provide only two-dimensional sites. In other words, the present oxygen sensor can conduct the reactions much more smoothly.

Since the present mixed conductor is porous, it can have a larger adsorption area for oxygen molecules. Thus, the adsorption reaction can be accelerated. In the present invention, the mixed conductor has an electron conductivity substantially equivalent to the oxygen ion conductivity. Thus, electrons generated at the electrode can be smoothly migrated to the oxygen atoms, resulting in acceleration of the ionization reaction. As the ionization reaction is accelerated, the dissociation reaction, that is, the preceding reaction, can also take place rapidly.

Furthermore, the mixed conductor has a higher oxygen ion conductivity than that of the solid electrolyte, and thus can transport the ionized oxygen to the solid electrolyte, thereby accelerating the leaving reaction.

On the other hand, in the present invention the mixed conductor in contact with the anode is the same as that in contact with the cathode, and thus can easily adsorb the oxygen ions migrated from the solid electrolyte. Electrons are discharged from the oxygen ions to form oxygen molecules. The discharged electrons are rapidly given to the electrode.

By providing a mixed conductor between each of the electrodes and the solid electrolyte, the electrochemical reactions can take place smoothly in a three-dimensional manner. That is, the electrochemical reactions can easily proceed even at such a low temperature as about 500° C. Thus, the present oxygen sensor can practically work even at such a low temperature. Thus, the present invention can provide an oxygen sensor capable of accelerating electrochemical reactions and working practically even at a low temperature.

BRIEF DESCRIPTION OF THE DRAWINGS

FIGS. 12A, 12B and 12C show working mechanisms of an oxygen sensor of prior art.

FIG. 13 shows electrochemical reactions of an oxygen sensor.

FIG. 14 is a sketch showing the state of ternary phase boundary points between electrode, solid electrolyte and gas phase according to prior art.

DETAILED DESCRIPTION OF PREFERRED EMBODIMENTS

EXAMPLE 1

An oxygen sensor according to one embodiment of the present invention will be described below, referring to FIGS. 1, 2, and 3A and 3B.

An oxygen sensor of Example 1 has a solid electrolyte 5, an outer electrode (cathode) 31 and an inner electrode (anode) 32, provided on the outer surface and the inner surfaces of the solid electrolyte 5, respectively. Mixed conductors 11 and 12 serving to adsorb oxygen molecules and conduct an ionization reaction are provided between the solid electrolyte 5 and the outer electrode 31 and between the solid electrolyte 5 and the inner electrode 32, respectively. The mixed conductors 11 and 12 are porous and have a higher oxygen ion conductivity than that of the solid electrolyte 5, and an electron conductivity substantially equivalent to the oxygen ion conductivity.

As the mixed conductors 11 and 12, a fluorite type oxide is used. More specifically, the fluorite type oxide used in Example 1 is $(CeO_2)_{0.915}(Y_2O_3)_{0.08}(Nb_2O_5)_{0.005}$. The mixed conductors 11 and 12 have a porosity of 30% and a layer thickness of 5 to 10 $\mu$m.

As the outer electrode 31 and the inner electrode 32, porous platinum electrodes are used, and $ZrO_2$ is used as the solid electrolyte.

In summary, conductivity A of the solid electrolyte, ion conductivity B and electron conductivity C of the mixed conductors and electron conductivity D of the electrodes have the following relationships: $A<B$, $B=C$, and $C<D$.

Figure 1:
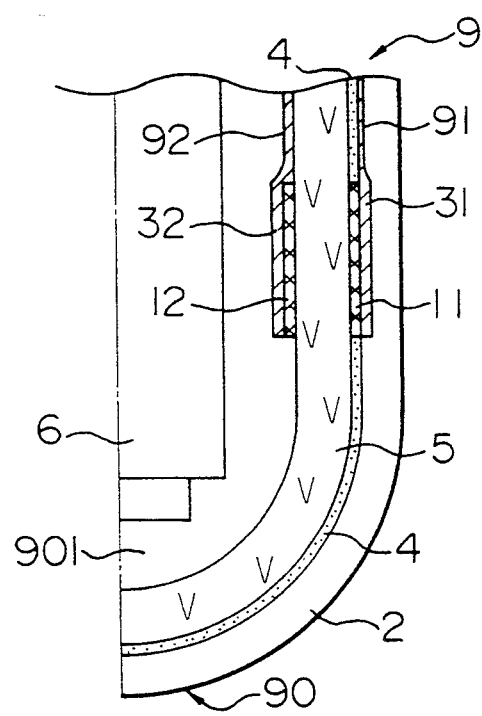
FIG. 1 is a cross-sectional view of the essential part of an oxygen sensor of Example 1 according to the present invention.
Figure 2:
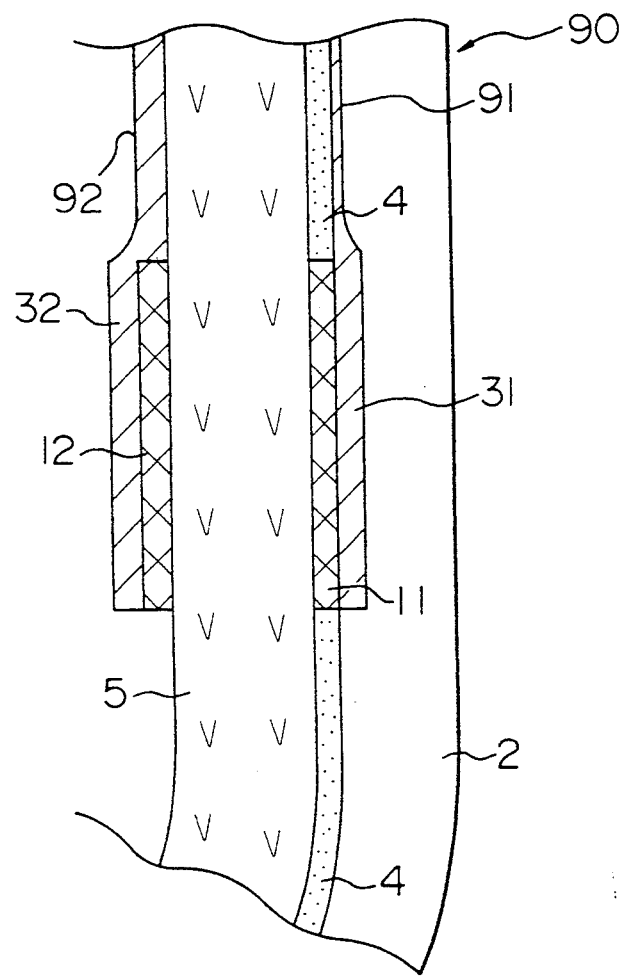
FIG. 2 is an enlarged cross-sectional view of the essential part of FIG. 1.

The oxygen sensor 9 of Example 1 is of limited current type, and has a sensor element 90 at the tip end. The sensor element 90 is a cup-formed element, as shown in FIGS. 1 and 2, and comprises the inner electrode 32, the solid electrolyte 5, the outer electrode 31, and a diffusion-resistant layer 2, provided from the inside outwardly by lamination. A heater 6 is inserted into the inner cavity of the sensor element 90.

The diffusion-resistant layer 2 is made of an insulator and is porous, and covers all the surfaces of the outer electrode 31 and an insulating layer 4. The insulating layer 4 is provided between the outer pheriphery of the solid electrolyte 5 and the diffusion-resistant layer 2 except for the site for the outer electrode 31. The outer electrode 31 and the inner electrode 32 are connected to a connector above the sensor element 90 through lead wires 91 and 92, respectively. Other members are the same as in prior art.

Figure 3A:
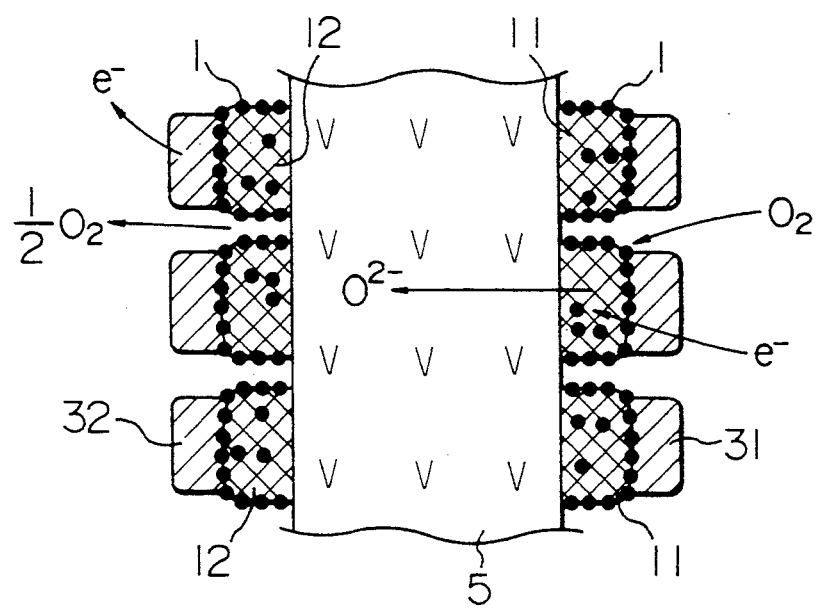
FIGS. 3A and 3B are sketches showing working mechanisms of the mixed conductor in the oxygen sensor of Example 1.

Working mechanisms and effects of the oxygen sensor of Example 1 will be described below:

In the oxygen sensor of this Example, the mixed conductors 11 and 12 are provided between the solid electrolyte 5 and the outer electrode (cathode) 31 and between the solid electrolyte 5 and the inner electrode (anode) 32, respectively, as shown in FIG. 3A. When the oxygen sensor is placed in an oxygen gas-containing atmosphere, oxygen molecules ($O_2$) are permeated into the mixed conductor 11 in contact with the outer electrode 31. The permeated oxygen molecules ($O_2$) are adsorbed in the mixed conductor 11, and the adsorbed oxygen molecules ($O_2$) are dissociated into oxygen atoms (O), while maintaining the adsorbed state. The dissociated oxygen atoms receive electrons ($e^-$) from the outer electrode 31 and are ionized, while leaving the mixed conductor 11 as oxygen ions ($O_{2-}$).

Figure 3B:
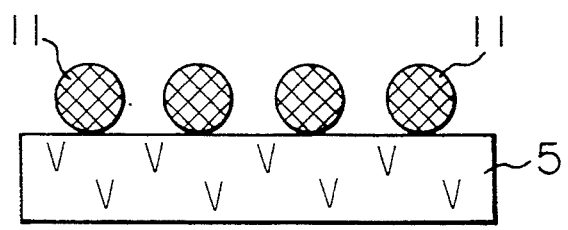

In this Example, a series of reactions such as adsorption reaction, dissociation reaction, ionization reaction and leaving reaction, proceed not only on the surface of the mixed conductor 11, but also inside it. That is, the three-phase boundary points 1 for the reactions (between the outer electrode or the inner electrode, the gas phase and the solid electrolyte) are formed inside the mixed conductors 11 and 12. Thus, the reactions take place at every sites in the mixed conductors, as shown in FIG. 3B, that is, at three-dimensional sites. Thus, in the oxygen sensor of this Example, the reactions take place much more and smoothly.

Since the mixed conductor 11 is porous and thus has a large adsorption area for oxygen molecules, the adsorption reaction can be accelerated.

The mixed conductor 11 has an electron conductivity substantially equivalent to the oxygen ion conductivity, and thus can transport the electrons generated at the electrode smoothly to the oxygen atoms. That is, the ionization reaction can be accelerated. As the ionization reaction is accelerated, the dissociation reaction, that is, the preceding reaction, can take place rapidly.

The mixed conductor 11 has a higher oxygen ion conductivity than that of the solid electrolyte 5, and thus the ionized oxygen can be easily migrated into the solid electrolyte 5. That is, the leaving reaction can be also accelerated.

In this manner, a series of 4 reaction steps can proceed in the mixed conductor 11 of this Example. The adsorption reaction, which is a rate-determining one of the electrochemical reactions, takes place rapidly. Therefore, by the above-mentioned fast reaction, the electrochemical reactions take place smoothly.

The mixed conductor 12 (anode) provided between the inner electrode 32 and the solid electrolyte 5 is the same as the mixed conductor 11 provided on the outer electrode (cathode) side and has three-phase boundary points 1 on the surface and inside thereof as contact points between the inner electrode 32, the solid electrolyte and the gas phase. Thus, the mixed conductor 12 can adsorb the oxygen ions ($O_{2-}$) migrated from the solid electrolyte 5 easily, and discharge electrons ($e^-$) from the oxygen ions ($O_{2-}$) to form oxygen molecules ($O_2$). The discharged electrons ($e^-$) are rapidly given to the inner electrode 32.

In the mixed conductors 11 and 12 of this Example, electrochemical reactions take place smoothly on both outer electrode 31 and inner electrode 32. Thus, the present oxygen sensor can work sufficiently even at a temperature of about 500° C. Thus, the oxygen sensor of this Example can practically work at such a low temperature.

EXAMPLE 2

In this Example, a process for producing the oxygen sensor of Example 1 will be described below, referring to FIGS. 4A and 4B.

Figure 4A:
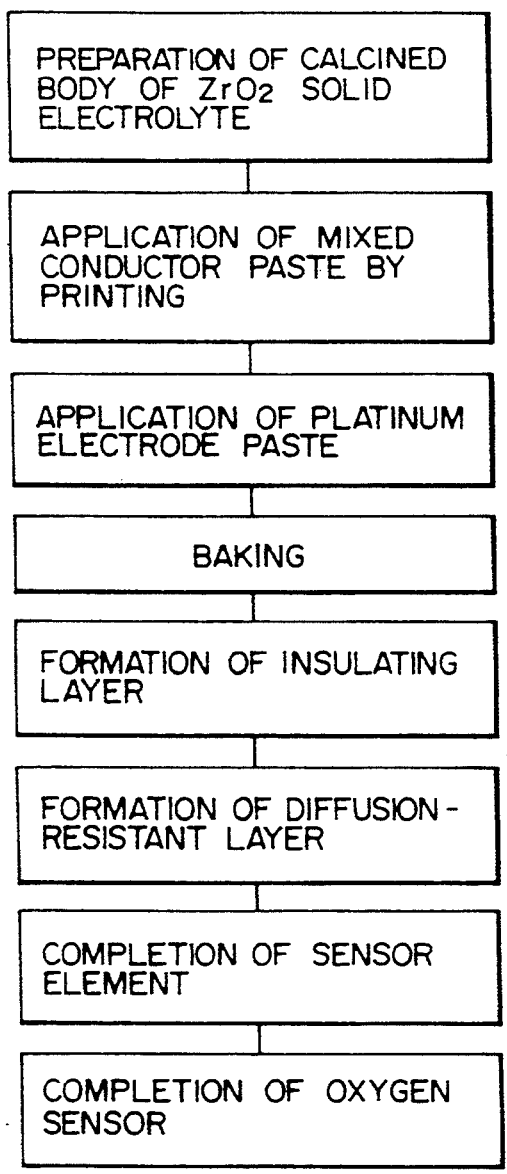
FIGS. 4A and 4B are block diagrams showing process steps for producing an oxygen sensor of Example 2 according to the present invention.

As shown in FIG. 4A, a $ZrO_2$ solid electrolyte paste is molded into a cup form, and the molding is fired at 1,300° C. to 1,500° C. to prepare a calcined body of $ZrO_2$ solid electrolyte.

Separately, a mixed conductor paste is prepared in the following manner. At first, a predetermined amount of acetates of metallic elements, Ce, Gd and Nb for constituting the mixed conductor is dissolved in a predetermined amount of water and dried and solidified in a rotary evaporator at about 60° C. to about 100° C. under reduced pressure. The resulting solidified dry product is heated to 200° C. to decompose the acetates of the metallic elements. Then, the decomposition product is pulverized and calcined in air at 900° C. to 1,100° C. to obtain powder of mixed conductor. Then, the powder is made into a paste to obtain a mixed conductor paste.

Then, the thus prepared mixed conductor paste is applied to both surfaces at predetermined area of the calcined body of the $ZrO_2$ solid electrolyte to a layer thickness of about 1 μm by printing.

Then, a platinum electrode paste for electrodes is applied to the surface of the applied mixed conductor pastes on both sides. Then, the resulting calcined body of $ZrO_2$ solid electrolyte is heated to 800° C. to 1,200° C. to form the mixed conductors 11 and 12, the outer electrode 31 and the inner electrode 32 on the calcined body by baking, as shown in FIG. 2.

Then, the insulating layer 4 is formed on the area free of the mixed conductor 11 on the outer surface of the solid electrolyte 5. Then, the diffusion-resistant layer 2 is formed on the surfaces of the outer electrode 31 and the insulating layer 4 by melt injection, thereby obtaining the sensor element 90.

Figure 8:
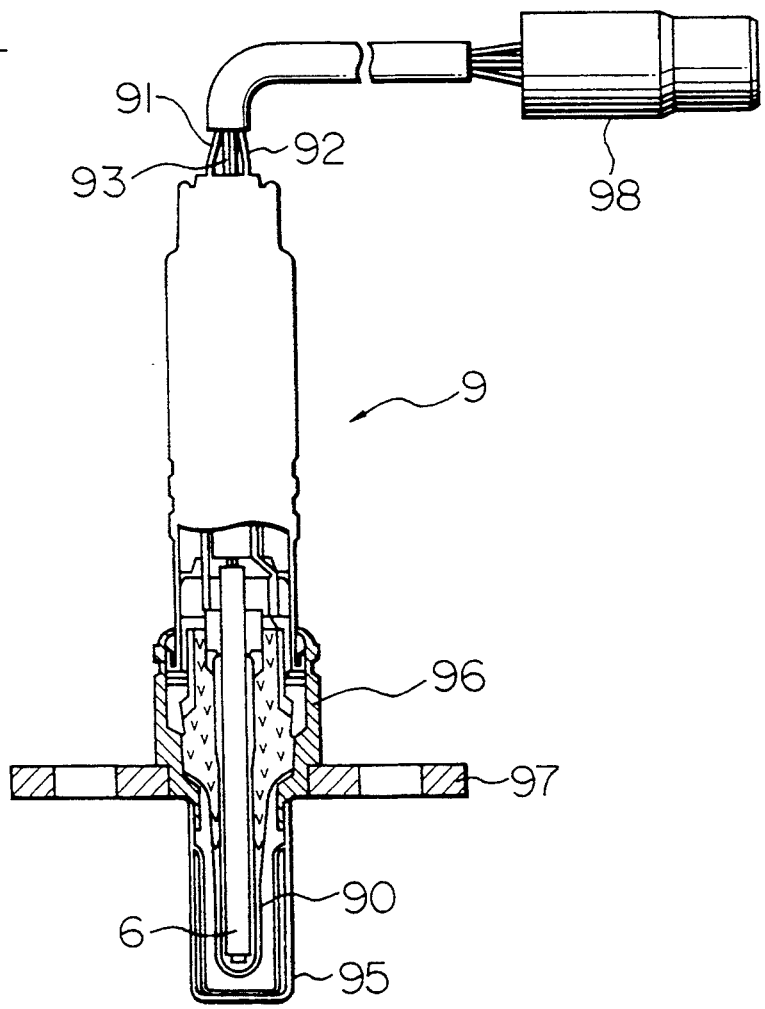
FIG. 8 is a cross-sectional, partly cut-away view of an oxygen sensor of prior art.
Figure 9:
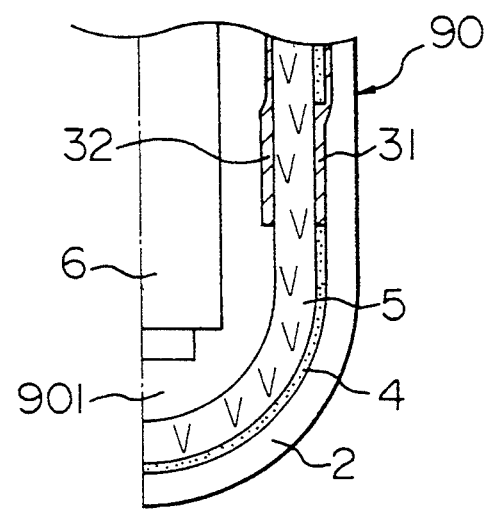
FIG. 9 is a cross-sectional view of the essential part of an oxygen sensor of prior art.
Figure 10:
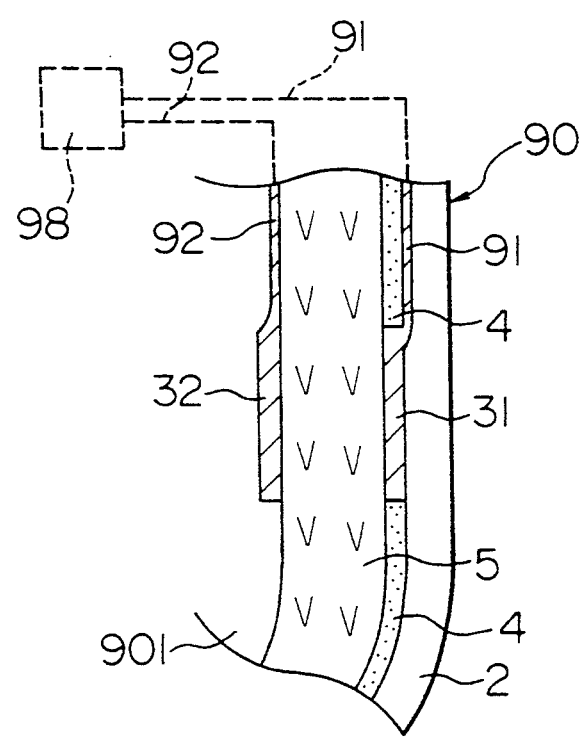
FIG. 10 is an enlarged cross-sectional view of the essential part of FIG. 8.
Figure 11:
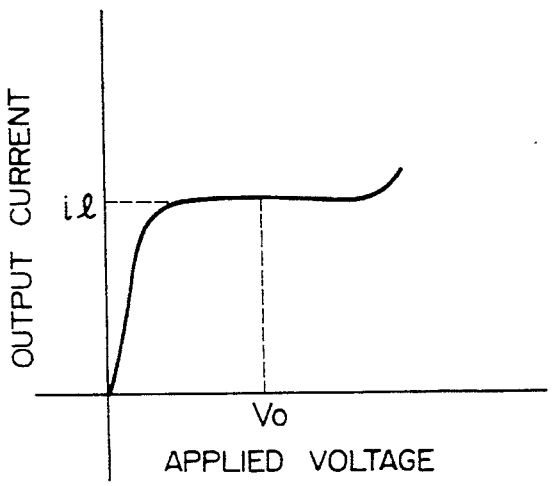
FIG. 11 is a chart showing relations between the applied voltage and the output current of an oxygen sensor of limited current type.
Figure 12A:
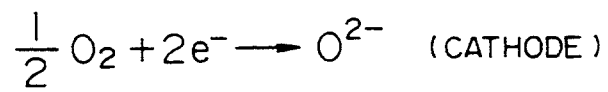
Figure 12A:
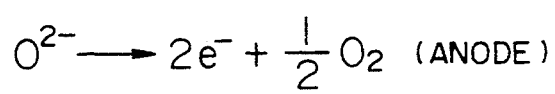
Figure 12B:
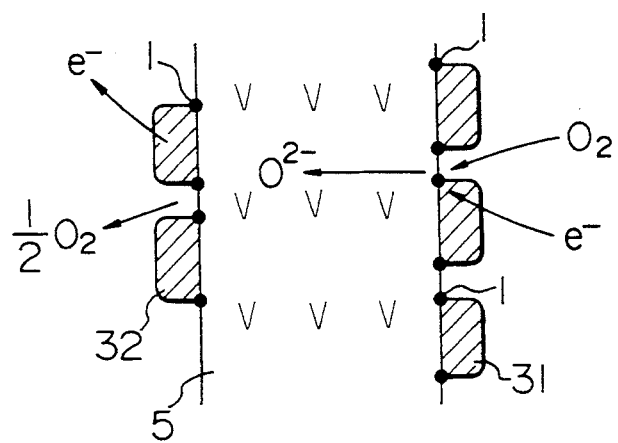

Then, the heater 6 is inserted into the inner cavity 901 of the sensor element 90 to complete the oxygen sensor, as in FIGS. 1 and 8.

Figure 4B:
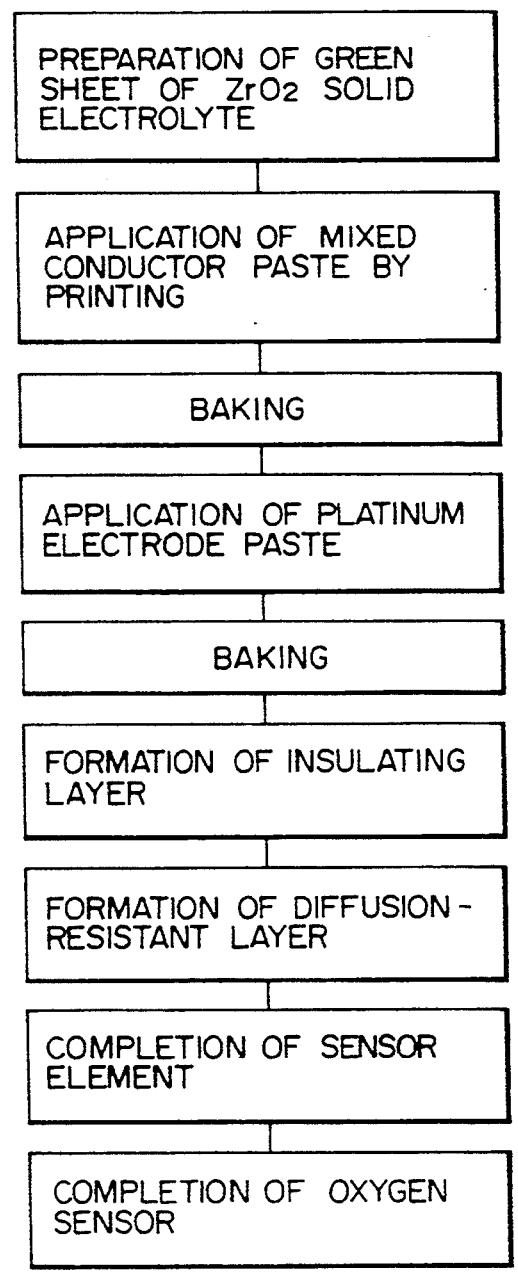

As an alternative process of the foregoing process, the mixed conductor paste for the mixed conductors 11 and 12 can be applied to predetermined areas on both surfaces of a solid electrolyte green sheet, and calcined, and then the platinum electrode paste can be applied thereto, followed by baking, as shown in FIG. 4B.

EXAMPLE 3

In an oxygen sensor of this Example, a perovskite type oxide is used for mixed conductors. The perovskite type oxide for use in this Example has the following chemical composition:

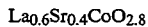

$La_{0.6}Sr_{0.4}CoO_{2.8}$

Other conditions are the same as in Example 1, and the same effects as in Example 1 can be obtained.

EXAMPLE 4

In this Example, relations between the working temperature and the output current were determined for the oxygen sensors of Examples 1 and 3 with an exhaust gas from an engine operated in an air/fuel ratio (A/F) of 25.

For comparison, the similar relations were determined for an oxygen sensor of prior art with no such mixed conductor.

Figure 5:
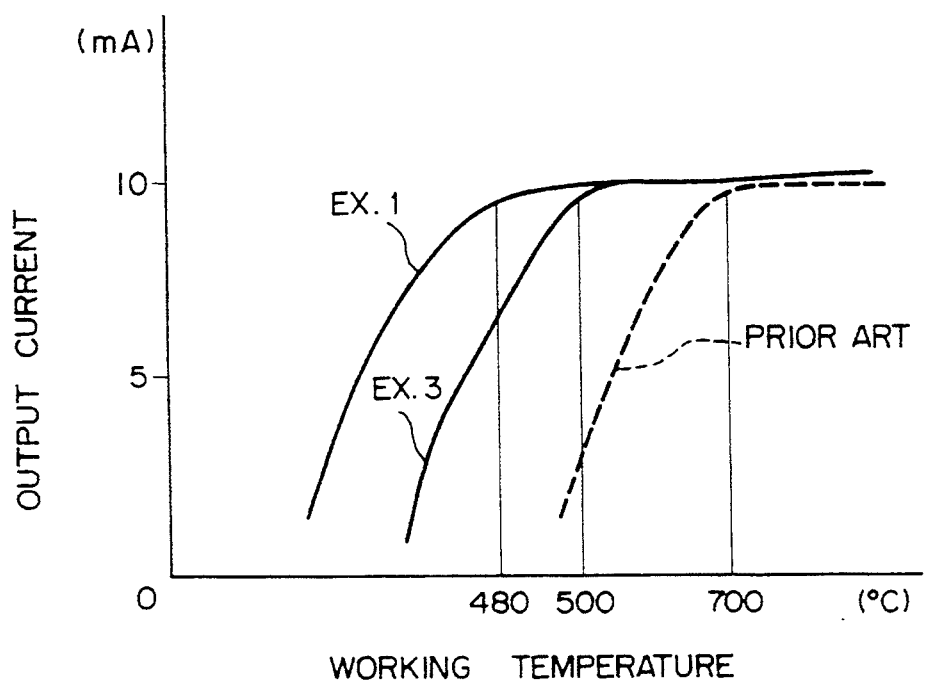
FIG. 5 is a chart showing relations between the working temperature and the output current of an oxygen sensor of Example 4 according to the present invention.

The results are shown in FIG. 5.

As is apparent from FIG. 5 the oxygen sensor of Example 1 had a stable output current at 480° C. and that of Example 3 had a stable output current at 500° C., while the oxygen sensor of prior art had a stable output current at such a high temperature as 700° C. This shows that in the oxygen sensors of the present invention the electrochemical reactions proceeded smoothly without any trouble even at a low temperature such as about 500° C.

EXAMPLE 5

Figure 6:
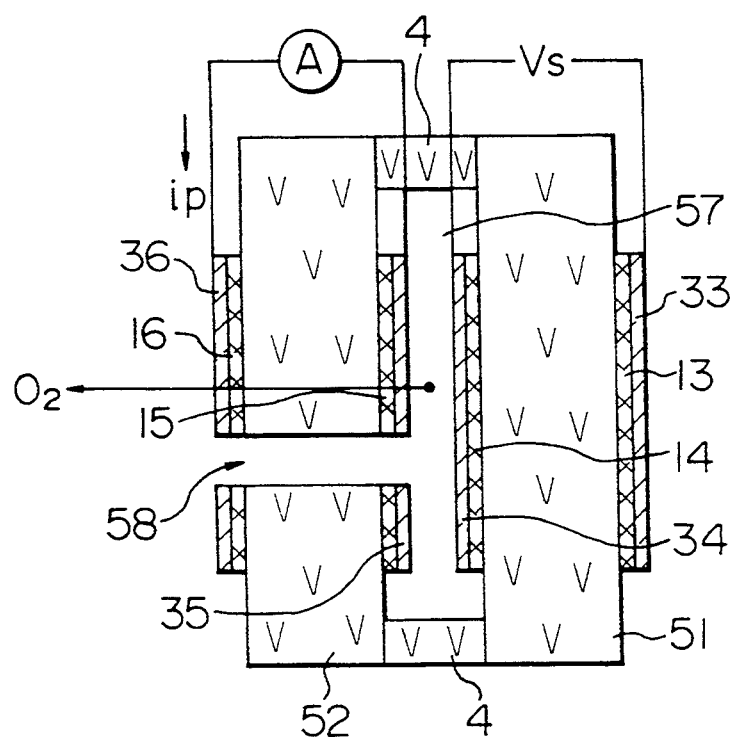
FIG. 6 is a cross-sectional view showing working mechanisms of an oxygen sensor of Example 5 according to the present invention.

In this Example, an oxygen sensor of $O_2$ pumping current type according to the present invention will be explained below, referring to FIGS. 6 and 7.

The oxygen sensor has two solid electrolytes 51 and 52, and an outer electrode (cathode) 33 and an inner electrode (anode) 34 are provided on the outer surface and the inner surface of the solid electrolyte 51, respectively, while an outer electrode (cathode) 36 and an inner electrode (anode) 35 are provided on the outer surface and the inner surface of the solid electrolyte 52. A first mixed conductor 13 is provided between the solid electrolyte 51 and the outer electrode 33, a second mixed conductor 14 between the solid electrolyte 51 and the inner electrode 34, a third mixed conductor 15 between the solid electrolyte 52 and the inner electrode 35, and a fourth mixed conductor 16 between the solid electrolyte 52 and the outer electrode 36. Insulators 4 are provided between the solid electrolytes 51 and 52 at both ends to form a cavity 57. A pinhole 58 is provided through the solid electrolyte 52.

Oxygen molecules ($O_2$) flowing in or out of the cavity 57 through the pinhole 58 are compensated by a corresponding quantity of pumping current so that an electromotive force $V_s$ between the electrodes 33 and 34 on the solid electrolyte 51 may be constant, thereby keeping the oxygen partial pressure in the cavity 57 constant. The pumping current flows when the oxygen ions ($O^{2-}$) migrate through the solid electrolyte 52, and the oxygen ions ($O_{2-}$) give electrons ($e^-$) to the electrode 35 or 36 while the oxygen ions ($O_{2-}$) migrate through the solid electrolyte 52 between the electrodes 35 and 36, whereby oxygen molecules ($O_2$) are formed. Thus, a current iP can flow between the electrodes 35 and 36. By detecting this output current A, an oxygen can be determined.

Figure 7:
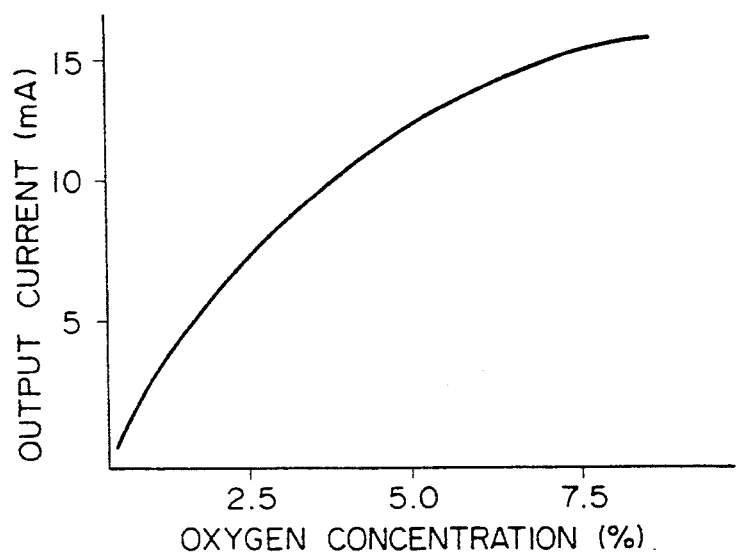
FIG. 7 is a diagram showing relations between the oxygen concentration and the output current of an oxygen sensor of $O_2$ pumping current type of Example 5.

In FIG. 7, relations between the oxygen concentration on the exhaust gas side and the output current iP flowing between the electrodes 35 and 36 are shown.

Other conditions are the same as in Example 1. The oxygen sensor of $O_2$ pumping current type of this Example can attain the same distinguished effects as in Example 1.

As shown in the foregoing Examples a mixed conductor is provided between the solid electrolyte and each of the electrodes. When electrodes are made of a mixed conductor, the electrodes will have a higher resistivity because the mixed conductor is made of an oxide and thus detection signals will be lowered. In the present invention, electrodes play a role of current collectors as in a cell.

What is claimed is:

1. An oxygen sensor which comprises a solid electrolyte and electrodes provided on both surfaces of the solid electrolyte, wherein a mixed conductor which functions to absorb oxygen molecules and conduct an ionization reaction of absorbed oxygen molecules is provided between the solid electrolyte and each of the electrodes.

2. An oxygen sensor according to claim 1, wherein the mixed conductor is porous and has a higher oxygen ion conductivity than that of the solid electrolyte and an electron conductivity substantially equivalent to the oxygen ion conductivity.

3. An oxygen sensor according to claim 2, wherein the mixed conductor is made of an oxide having a perovskite structure or an oxide having a fluorite structure.

4. An oxygen sensor which comprises a solid electrolyte and electrodes provided on both surfaces of the solid electrolyte, wherein a mixed conductor which functions to absorb oxygen molecules and conducts an ionization or deionization reaction of oxygen molecules or oxygen ions is provided between the solid electrolyte and each of the electrodes and wherein the electrodes function only to conduct the molecular oxygen gas and electrons.

5. An oxygen sensor according to claim 4, wherein the mixed conductor is porous and has a higher oxygen ion conductivity than that of the solid electrolyte and an electron conductivity substantially equivalent to the oxygen ion conductivity.

6. An oxygen sensor according to claim 5, wherein the mixed conductor is made of an oxide having a perovskite structure or an oxide having a fluorite structure.

7. An oxygen sensor which comprises a solid electrolyte and electrodes provided on both surfaces of the solid electrolyte, wherein a mixed conductor which functions to absorb oxygen molecules and conduct an ionization or deionization reaction of oxygen molecules or oxygen ions is provided between the solid electrolyte and each of the electrodes and wherein the electrodes function only to conduct the molecular oxygen gas and electrons, and wherein in conductivity A of the solid electrolyte, ion conductivity B and electron conductivity C of the mixed conductors and electron conductivity D of the electrodes have the following relationships:

$$A < B$$

$$B \approx C, \text{ and } C << D.$$

8. An oxygen sensor according to claim 7, wherein the mixed conductor is made of an Oxide having a perovskite structure or an oxide having a fluorite structure.

* * * * *